United States Patent
Foster et al.

(10) Patent No.: US 11,583,253 B2
(45) Date of Patent: Feb. 21, 2023

(54) DUAL FREQUENCY PLANE WAVE ULTRASOUND IMAGING SYSTEM

(71) Applicants: FUJIFILM SonoSite, Inc., Bothell, WA (US); Sunnybrook Research Institute, Toronto (CA)

(72) Inventors: F. Stuart Foster, Toronto (CA); Desmond Hirson, Thornhill (CA); Nicholas Christopher Chaggares, Whitby (CA); Emmanuel W. Cherin, Toronto (CA); Jianhua Yin, Scarborough (CA); Jing Yang, Toronto (CA); Christine Demore, Toronto (CA)

(73) Assignees: FUJIFILM SONOSITE, INC., Bothell, WA (US); SUNNYBROOK RESEARCH INSTITUTE, Toronto (CA)

( * ) Notice: Subject to any disclaimer, the term of this patent is extended or adjusted under 35 U.S.C. 154(b) by 946 days.

(21) Appl. No.: 16/115,325

(22) Filed: Aug. 28, 2018

(65) Prior Publication Data

US 2019/0069879 A1 Mar. 7, 2019

Related U.S. Application Data (60) Provisional application No. 62/553,497, filed on Sep. 1, 2017.

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/4477* (2013.01); *A61B 8/481* (2013.01);
(Continued)

(58) Field of Classification Search
CPC ..... A61B 8/4494; A61B 8/4477; A61B 8/481; A61B 8/5207; A61B 8/5246; A61B 8/14;
(Continued)

(56) References Cited

U.S. PATENT DOCUMENTS 6,186,951 B1 2/2001 Lizzi et al.
6,309,356 B1 * 10/2001 Ustuner ............. G01S 7/52026
600/443

(Continued)

FOREIGN PATENT DOCUMENTS

| CN | 203059751 U | 7/2013 |
| CN | 106 901 777 A | 6/2017 |
| WO | WO 2013/032946 A1 | 3/2013 |

OTHER PUBLICATIONS

International Search Report and Written Opinion dated Dec. 14, 2018 in International Application No. PCT/US2018/048401.
(Continued)

*Primary Examiner* — Carolyn A Pehlke
(74) *Attorney, Agent, or Firm* — Baker Botts L.L.P.

(57) ABSTRACT

A dual frequency transducer array includes one or more low frequency transducer arrays and a high frequency transducer array. Unfocused ultrasound such as plane waves are transmitted by the one or more low frequency transducer arrays in a number of different directions into an imaging region of the high frequency transducer array. High frequency echo signals produced by excited contrast agent in the imaging region are received by the high frequency transducer array to produce a contrast agent image. In another embodiment, the high frequency transducer produces unfocused ultrasound to excite the contrast agent in the imaging region and the low frequency transducer(s) receives low frequency echo signals from the excited contrast agent. A tissue image is created from echo signals received by the high or low frequency transducer. Echo data from the tissue image and the contrast agent image are combined to produce a combined tissue/contrast agent image.

20 Claims, 7 Drawing Sheets

(51) Int. Cl.
*A61B 8/14* (2006.01)
*G01S 15/89* (2006.01)
*G01S 7/52* (2006.01)

(52) U.S. Cl.
CPC .......... *A61B 8/5207* (2013.01); *A61B 8/5246* (2013.01); *G01S 7/52039* (2013.01); *G01S 7/52074* (2013.01); *G01S 15/8952* (2013.01); *G01S 15/8995* (2013.01); *A61B 8/14* (2013.01); *G01S 15/8915* (2013.01)

(58) Field of Classification Search
CPC .... A61B 8/06; A61B 8/00; A61B 8/13; A61B 8/4455; A61B 8/4444; G01S 15/8927; G01S 15/8952; G01S 15/895; G01S 15/8913; G01S 15/8911; G01S 15/8909; G01S 15/8929
See application file for complete search history.

(56) References Cited

U.S. PATENT DOCUMENTS

| | | | |
|---|---|---|---|
| 6,312,383 B1 | 11/2001 | Lizzi et al. | |
| 6,726,629 B1 * | 4/2004 | Frinking | G01S 15/8952 600/458 |
| 9,532,769 B2 | 1/2017 | Dayton et al. | |
| 2001/0001108 A1 | 5/2001 | Lizzi et al. | |
| 2003/0055337 A1 * | 3/2003 | Lin | G01S 15/8915 600/459 |
| 2004/0158154 A1 * | 8/2004 | Hanafy | G01S 15/8993 600/446 |
| 2004/0267129 A1 | 12/2004 | Angelsen | |
| 2007/0038082 A1 * | 2/2007 | Mo | G01S 15/8952 600/437 |
| 2008/0200813 A1 | 8/2008 | Quistgaard | |
| 2009/0299189 A1 | 12/2009 | Yeh et al. | |
| 2010/0262013 A1 * | 10/2010 | Smith | A61B 8/4218 600/459 |
| 2012/0095699 A1 * | 4/2012 | Angelsen | G01S 15/8952 702/33 |
| 2012/0220869 A1 | 8/2012 | Dayton et al. | |
| 2013/0253325 A1 | 9/2013 | Call et al. | |
| 2017/0343656 A1 * | 11/2017 | Angelsen | G01S 15/8929 |

OTHER PUBLICATIONS

Extended European Search Report dated Apr. 13, 2021 in Application No. EP 18852530.

Couture et al., "Ultrasound Contrast Plane Wave Imaging," IEEE Transactions on Ultrasonics, Ferroelectrics, And Frequency Control, 59(12):2676-2683 (2012).

* cited by examiner

DUAL FREQUENCY PLANE WAVE ULTRASOUND IMAGING SYSTEM

RELATED APPLICATIONS

The present application is related to, and claims the benefit of, U.S. Provisional Patent Application No. 62/553,497, filed Sep. 1, 2017, which is hereby incorporated by reference in its entirety.

STATEMENT REGARDING FEDERALLY SPONSORED RESEARCH OR DEVELOPMENT

This disclosure was made with government support under grant number 5100220 awarded by National Institutes of Health (NIH)—Federal Reporting and grant number RO1CA189479. The government has certain rights in the invention.

TECHNICAL FIELD

The disclosed technology relates generally to ultrasound imaging systems and in particular to systems for imaging using contrast agents.

BACKGROUND

As will be appreciated by those skilled in the art, most modern ultrasound imaging systems work by creating acoustic ultrasound signals (i.e. pressure waves) from a number of individual transducer elements that are formed in a sheet of piezoelectric material. By applying a voltage pulse across an element, the element is physically deformed thereby generating a corresponding ultrasound signal. The signal travels into a region of interest where a portion of the signal is reflected back to the transducer as an acoustic echo signal. When an echo signal impinges upon a transducer element, the element is vibrated, causing a corresponding voltage to be created that is detected as an electronic signal. Electronic signals from multiple transducer elements are combined and analyzed to determine characteristics of the combined signal such as its amplitude, frequency, phase shift, power and the like. The characteristics are quantified and converted into pixel data that are used to create an image.

In some environments, it is desirable to increase the contrast of the tissue being imaged. This is particularly true when obtaining images of blood vessels and blood flow. To increase the contrast, intravascular contrast agents are often administered in the blood vessels. Such contrast agents generally comprise lipid or protein encapsulated microbubbles that travel through the circulatory system and have an acoustic impedance that is approximately four orders of magnitude less than the surrounding tissue. This large acoustic impedance mismatch allows the microbubbles to been seen clearly in an ultrasound image.

In some systems, contrast agents are insonified and imaged in the same frequency band. For example, low frequency ultrasound (e.g. 1-5 MHz) is directed into the subject and corresponding echo signals in the same frequency band are detected and used to produce a tissue image. One problem with this method is that because the transmitted and received ultrasound signals are in the same frequency band, it is often difficult to distinguish between soft tissue backscatter and backscatter from the contrast agent in the blood vessels, unless a significant amount of contrast agent is supplied to make the signal from the blood vessels stronger than the signal from the tissue. To overcome this problem, it is also known that the insonification of the contrast agent and the detection of the ultrasound echoes from the contrast agent can be performed in different frequency bands. Because the contrast agent has a non-linear response to applied ultrasound, it is possible to insonify the contrast agent in one frequency band and analyze harmonics or subharmonics of the excitation frequency to image the contrast agent. Harmonic imaging where ultrasound excitation signals are applied in a relatively low frequency range (e.g. 1-5 MHz) and the generated echo signals are analyzed with the same transducer to extract the harmonic component of the signal is a known technique to enhance the microbubble contrast signal relative to the tissue signal.

For many applications, the frame rates at which harmonic images can be produced by traditional line-based imaging are insufficient to allow quickly moving tissue structures to be adequately captured by an ultrasound imaging system. Plane wave imaging is a technique whereby unfocused ultrasound is transmitted into the body over a large portion of a region of interest at once and the corresponding echo signals are simultaneously received at multiple transducer elements. The received echo signals are beamformed to produce images of the region of interest at high frame rates. Image quality can be improved while still maintaining fairly high frame rates by steering the plane waves in several directions and combining the echo data using a spatio-temporal beamformer to produce a composite image of the tissue.

SUMMARY

The disclosed technology is a system and method for imaging tissue and ultrasound contrast agents at high frame rates. As will be explained, a dual frequency ultrasound transducer has one or more low frequency transducers for producing ultrasound to excite a contrast agent and a high frequency transducer for receiving higher frequency ultrasound echo signals produced by the excited contrast agent. In one embodiment, an ultrasound system transmits unfocused ultrasound such as plane waves from a low frequency transducer in a number of different directions and the high frequency transducer receives echo signals from the contrast agent in each direction. Echo data produced from the contrast agent are beamformed and then combined with echo data from tissue to produce images showing both tissue and contrast agent. The tissue images can be produced by transmitting and receiving from the low frequency transducer and/or transmitting and receiving from the high frequency transducer.

In another embodiment, the high frequency transducer is used to transmit unfocused ultrasound such as plane waves in a number of different directions and the low frequency transducer receives echo signals from the contrast agent at subharmonics of the transmit frequency in each direction. Echo data received by the low frequency transducer are beamformed to produce the contrast agent image and can be combined with echo data for high or low frequency B-mode images to form a complete image of tissue and vasculature.

In one embodiment, a dual frequency transducer includes a high frequency transducer array that is flanked by one or more low frequency transducer arrays that are oriented to direct unfocused transmissions into an imaging region covered by the high frequency transducer array. Echo data from high frequency echo signals created in response to the transmissions from the one or more flanking low frequency transducer arrays are combined with echo data representing tissue to produce an image showing both tissue and the contrast agent.

DETAILED DESCRIPTION

Figure 1:
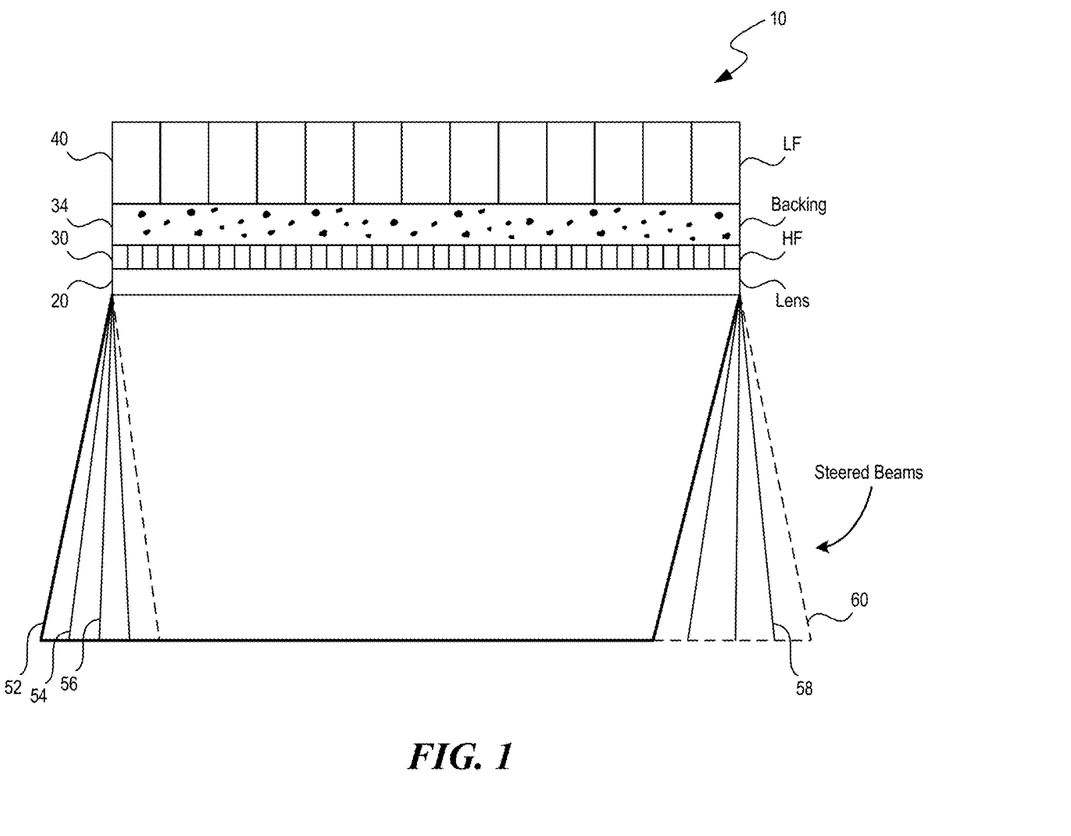
FIG. 1 is a partial schematic view of a dual frequency ultrasound transducer in accordance with an embodiment of the disclosed technology.

As shown in FIG. 1, a dual frequency ultrasound transducer 10 includes a high frequency transducer array 30 and a low frequency transducer array 40 that is positioned behind or proximal to the high frequency array. A fixed lens 20 is positioned in front of the high frequency transducer array 30 to focus the transducer elements of the high frequency transducer array in an imaging region. The lens 20 is connected to the high frequency transducer array 30 through one or more matching layers (not shown). An intermediate backing/matching layer 34 is positioned between the high frequency transducer array 30 and the low frequency transducer array 40 that serves to match the impedance of the low frequency transducer array to the elements that are distal to the low frequency transducer array and to absorb high frequency ultrasound energy. The intermediate backing/matching layer 34 is preferably about a quarter wavelength thick (or an odd multiple thereof) at the transmit frequency and the speed of sound in the tissue to be insonified and should absorb the high frequency signals from the contrast agent and from the HF transducer (if used to transmit). Suitable materials for the intermediate backing/matching layer 34 can include particle loaded epoxies or silicone-based materials. In one embodiment, a suitable intermediate backing/matching layer is made of EPO-TEK 301 epoxy doped with particles that absorb high frequency ultrasound and pass low frequency ultrasound such, as but not limited to, silica, alumina, tungsten, PZT or silicone.

As will be appreciated by those skilled in the art, the high and low frequency transducer arrays can be formed in a sheet of piezoelectric material that is cut with a dicing saw or laser to produce a number of transducer elements. In one embodiment, the element size for the high frequency transducer array 30 is approximately 90 microns wide, while the size of the transducer elements in the low frequency transducer array 40 is approximately 720 microns. In one embodiment, the size of the elements in the low frequency transducer array 40 is selected with respect to the operating frequency of the transducer so that it can function as a phased array. By carefully selecting the phase and weights of the driving signals applied to the elements of the low frequency transducer array 40, unfocused ultrasound such as plane waves can be steered over a range of angles in the imaging region of the high frequency transducer.

As will be appreciated, the element size for the transducer elements in the low frequency transducer array is preferably about equal to the wavelength of the transmit frequency or less to minimize side lobe creation in the transmit plane waves. For example, a 720 micron transducer element size at 0.8 lambda implies a transmit frequency of 1.7 MHz—assuming a speed of sound of approximately 1520 m/s. A 90 micron element at a 1.25 lambda pitch for the high frequency transducer implies a transmit frequency of 21 MHz. In some embodiments, the high frequency transducer is designed to operate at a frequency of at least three times that of the low frequency transducer.

In one disclosed embodiment, the ultrasound transducer 10 is connected to an ultrasound imaging machine (not shown) that supplies driving signals to the elements to generate ultrasound signals and processes the electronic signals produced in response to the detected echo signals. In one embodiment, the transducer is controlled to emit ultrasound signals from all the transducer elements at nearly the same time so that unfocused ultrasound signals such as plane waves travel into the region of interest. The phase of the driving signals applied is controlled so that one or more plane waves are oriented left, right or straight ahead of the front face of the transducer in the imaging plane of the high frequency transducer array. In the embodiment shown in FIG. 1, unfocused ultrasound transmissions such as plane waves are transmitted in directions 52 and 54 that are on one side of a direction 56 that is straight out from, or normal to, the front face of the high frequency transducer array and can be transmitted in directions 58, 60 that are on the other side of the direction 56. Of course, by the appropriate phasing and element size for the low frequency transducer array, other transmit and receive angles are possible. In one embodiment, the unfocused ultrasound transmissions are plane waves. However, it will be appreciated that other unfocused transmissions such as spherical waves or other transmissions that simultaneously cover a substantial portion of the imaging region could be used.

The high frequency transducer array 30 includes an array of transducer elements that are focused in an imaging region by the lens 20. In one embodiment, the lens 20 is a fixed focus lens made of a polymer such as TPX™ polymethylpentene or a cross-linked polystyrene such as Rexolite™. The element size of the high frequency transducer array 30 is such that the transducer itself operates as a low pass filter preventing the high frequency ultrasound signals from reaching the low frequency transducer array while being responsive to ultrasound echo signals at a harmonic frequency of a transmitted plane waves.

Low frequency ultrasound plane waves are transmitted in a number of different directions and in one embodiment, the electronic echo signals produced by the high frequency transducer array in response to the low frequency plane waves are beamformed to produce a contrast agent image.

Figures 2A, 2B:
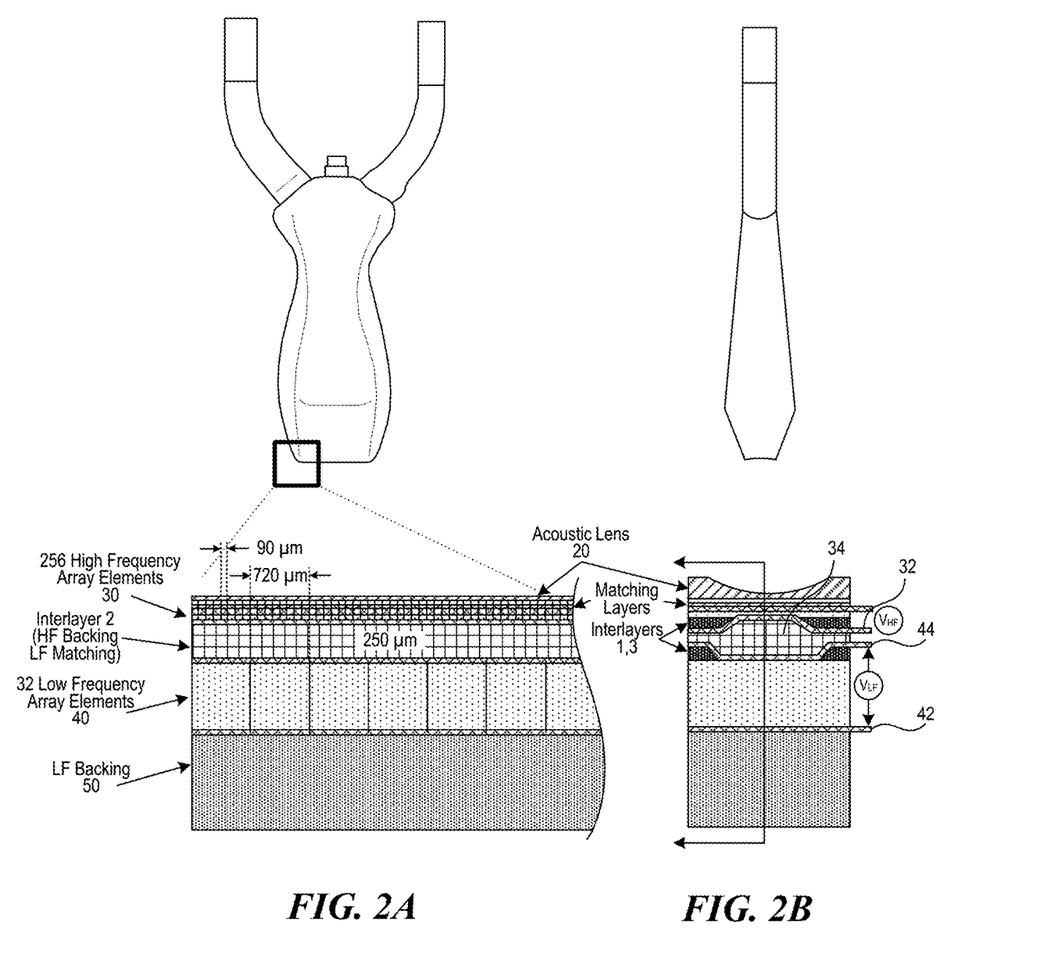
FIGS. 2A and 2B illustrate further detail of a dual frequency ultrasound transducer in accordance with an embodiment of the disclosed technology.

FIG. 2A shows additional detail of the dual frequency transducer shown in FIG. 1. In one embodiment, the high frequency transducer 30 comprises an array of 256 elements while the low frequency transducer 40 comprises an array of 32 elements. The element size of the low frequency transducer array is eight times larger than the element size of the high frequency transducer. However, other element sizes and array sizes could be used. The rear surface of the low frequency transducer array 40 is coupled to a backing layer 50 to prevent reflections of the transmitted plane waves and the corresponding low frequency echoes. In one embodiment, the low frequency and high frequency arrays are one dimensional arrays. However, it will be appreciated that other dimensions such as 1.5D or 2D arrays could be used.

In the embodiment shown in FIG. 2B, the transducer stack includes a number of electrode layers surrounding the high frequency and low frequency transducer elements. In the embodiment shown, the high frequency transducer array includes a ground electrode on the distal face of the array and a set of individual signal electrodes on a proximal side of the high frequency array. In one embodiment, the electrodes are made of gold or other conductive metal that is sputter coated onto the array. In some embodiments, the electrodes in the high frequency transducer array are made with a laser-etch-laser process as described in U.S. Patent Publication No. US2017/0144192A1 or U.S. Pat. Nos. 8,316,518 and 9,173,047, which are all herein incorporated by reference in their entireties.

In the cross-sectional view shown in FIG. 2B, one embodiment of the dual frequency transducer has the signal electrodes facing each other and the ground electrodes on the outsides of the stacked transducers. In the embodiment shown, the low frequency transducer array 40 includes a ground electrode 42 on a proximal surface and a number of signal electrodes 44 on a distal surface. The high frequency transducer array 30 includes a number of signal electrodes 32 adjacent the signal electrodes 44 for the low frequency transducer array and a ground electrode 34 on the distal surface of the dual frequency transducer array. Other configurations of the ground and signal electrodes are also possible such as having the ground electrodes of both transducers adjacent to each other or having the ground electrodes of both transducers on the distal side of the respective transducers or having the ground electrodes of both transducers on the proximal side of the respective transducers.

In some embodiments, the signal electrodes 44, 32 are in contact with the piezoelectric material that forms the transducer arrays in the active areas of the transducer and are separated from the piezoelectric material by an interlayer of silica doped epoxy that is adhered to the piezoelectric surface. The interlayer is formed to provide a smooth surface for the signal electrodes to transition to the surface of the piezoelectric material. In addition, because the capacitance of the piezoelectric material is so much greater than the capacitance of the interlayer, any voltage differential (e.g. a driving signal) applied between the signal electrode and the ground electrode is divided mostly across the interlayer so that there is little or no voltage drop across the piezoelectric material in the non-active areas of the transducer array.

Figure 3:
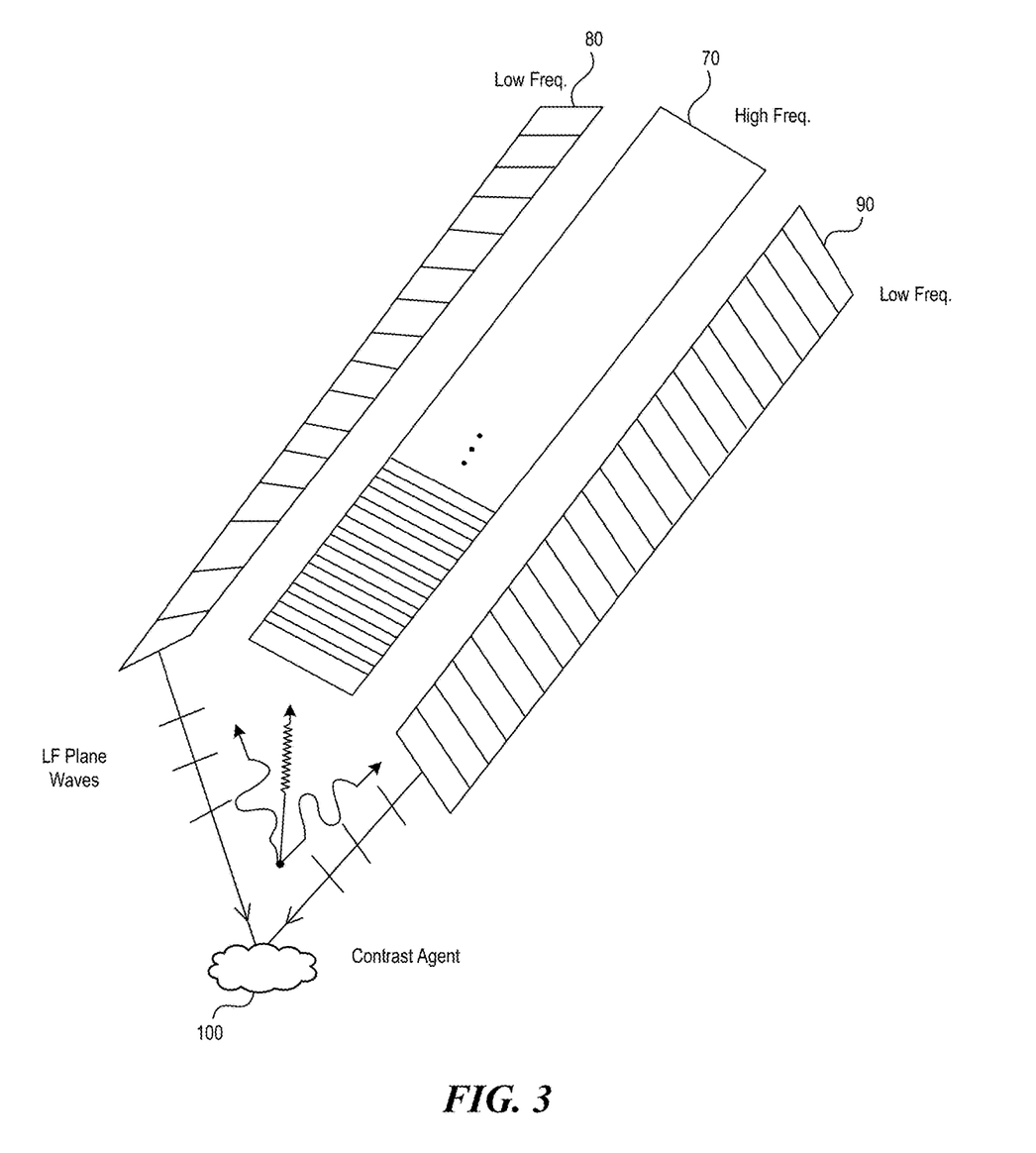
FIG. 3 illustrates a dual frequency ultrasound transducer with a center high frequency transducer array and one or more flanking low frequency transducer arrays in accordance with another embodiment of the disclosed technology.

FIG. 3 shows an alternative arrangement of a dual frequency transducer array constructed in accordance with another embodiment of the disclosed technology. In this embodiment, a high frequency transducer array 70 is flanked by one or more low frequency transducer arrays 80, 90 that are positioned so that unfocused ultrasound transmissions such as plane waves from the low frequency transducer array(s) intersect at an angle with the imaging region 100 of the high frequency transducer array 70. During use, a contrast agent is supplied to the area of the imaging region 100 and the one or more low frequency transducer arrays transmit plane waves directed at the contrast agent. Plane waves from the low frequency transducer array(s) insonify the contrast agent causing it to produce echo signals that are received by the high frequency transducer array. In one embodiment, echo data produced in response to the plane waves transmitted at different transmit directions are spatio-temporally beamformed to produce a contrast agent image that is combined with echo data for a tissue image to create a combined tissue/contrast agent image.

In one embodiment, the high frequency transducer array produces unfocused ultrasound transmissions such as plane wave signals that are transmitted into the subject and receives the corresponding echo signals to produce an image of tissue in a region of interest. The ultrasound plane waves can be transmitted in different directions and the echo data beamformed or compounded to produce a tissue image.

In one embodiment, the transmissions for imaging tissue are interleaved with the transmissions for insonifying the contrast agent so that the echo signals from the tissue do not interfere with those from the contrast agent. In another embodiment, the system transmits low frequency plane waves for exciting the contrast agent in multiple directions, stores the corresponding HF echo signals in a memory as the echo signals are received and performs spatio-temporal beamforming to create a contrast image frame. The HF transducer then creates HF plane waves that are transmitted in multiple directions, stores the corresponding echo signals in a memory as the corresponding echo signals are received and performs spatio-temporal beamforming to create the tissue image frame. Data from the contrast agent frame and the tissue frame are then combined to create a tissue/contrast image.

In some embodiments, the low frequency transducer(s) produce the transmissions that excite the microbubbles and the high frequency transducer captures the corresponding echo signals at a frequency that is higher than the excitation frequency. In another embodiment, the high frequency transducer produces the transmissions that excite the microbubbles and the low frequency transducer(s) capture the corresponding echo signals at a frequency that is lower than the transmit frequency.

Although transmissions for the contrast agent are preferably transmitted at different angles and the radio frequency (RF) echo data combined with spatio-temporal beamforming, it will be appreciated that contrast agent frames can be created from transmissions in a single direction and the data from multiple frames combined with compounding.

The tissue image (e.g. a B-mode image) can be produced by the low frequency transducer(s) transmitting and receiving at a low frequency or the high frequency transducer transmitting and receiving at a high frequency. The tissue image can be captured with planewave imaging techniques (e.g. spatio-temporal beamforming) or by line-based transmissions with delay and sum beamforming.

Echo data from the contrast agent image are combined with echo data from the tissue image to produce a combined tissue/contrast agent image. Because plane wave imaging techniques can be used to generate image frames at a rapid rate, the overall frame rate at which the combined tissue/contrast agent images are produced is sufficiently high to allow the system to capture quickly moving tissue or blood flow.

Figure 4:
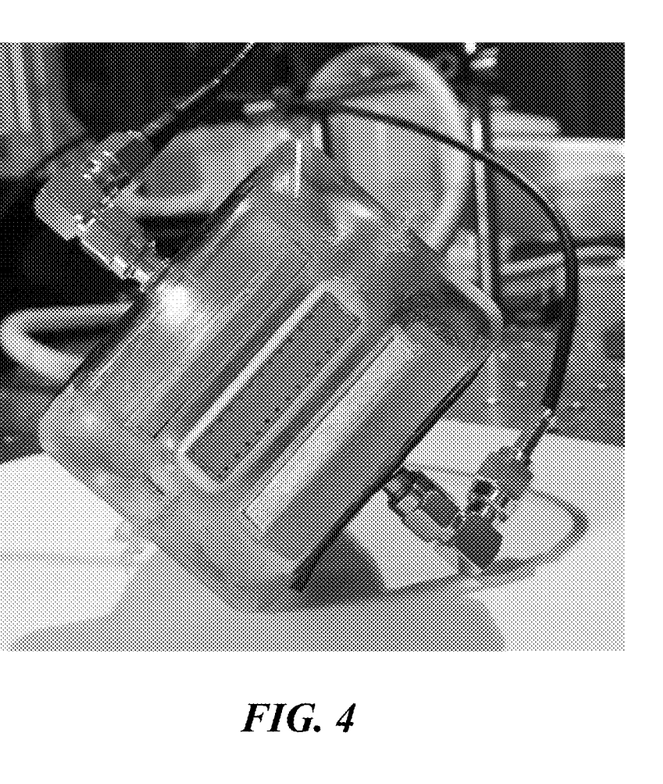
FIG. 4 is an image of a prototype dual frequency ultrasound transducer having a center high frequency transducer array and a pair of flanking low frequency transducer arrays in accordance with an embodiment of the disclosed technology.

FIG. 4 shows a prototype dual frequency transducer array with a central high frequency transducer array and a pair of flanking low frequency transducer arrays positioned to direct unfocused acoustic signals into the focal region of the high frequency array. The transducer arrays are held in an encapsulating plastic material. The encapsulating material holds the transducer arrays in their respective orientations and supports the electrical connections to the transducer electrodes.

Figure 5:
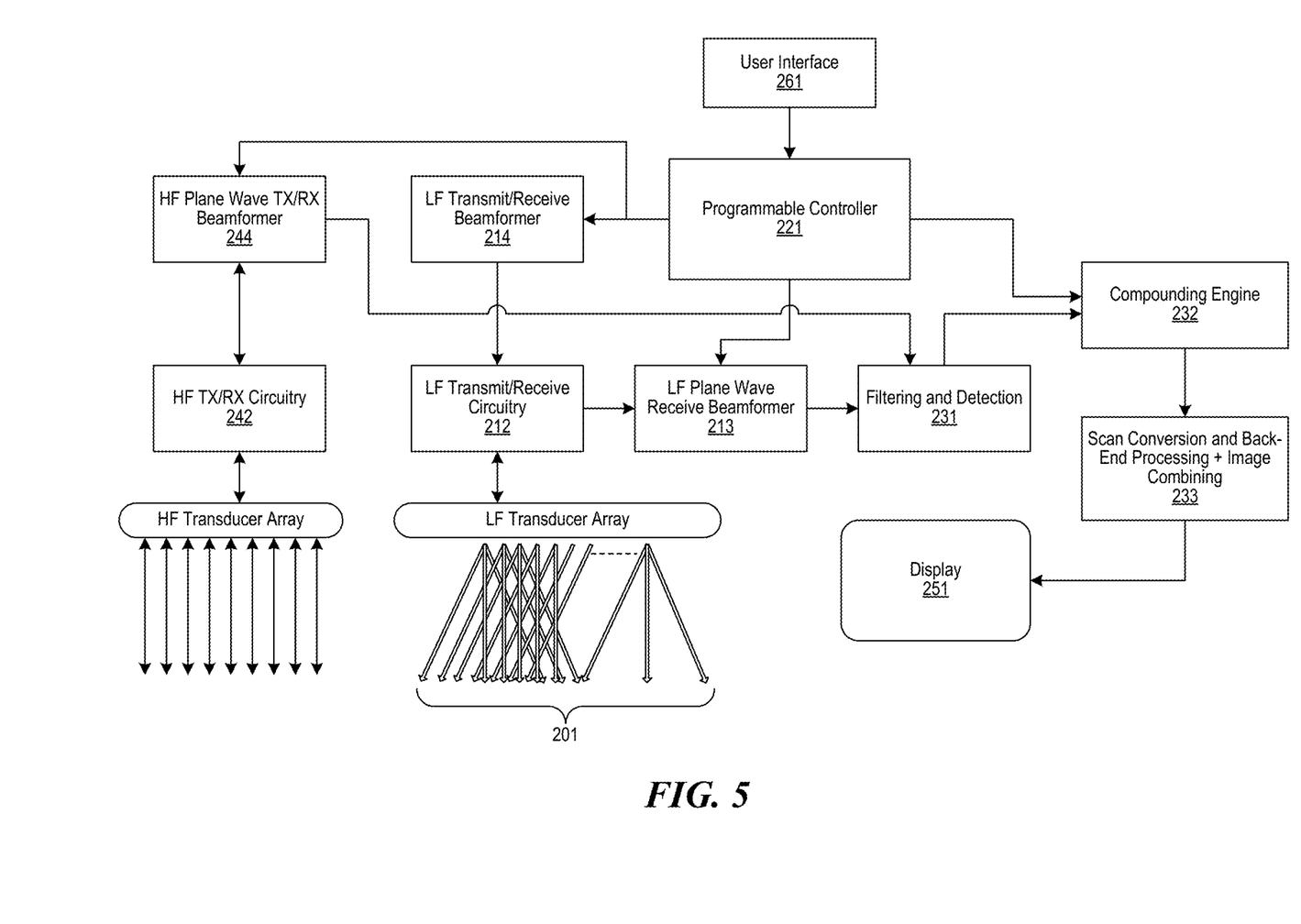
FIG. 5 is a block diagram of an ultrasound imaging machine configured to produce a combined tissue/contrast agent image in accordance with one embodiment of the disclosed technology.

Directing attention to FIG. 5, an ultrasound imaging system 200 is adapted to provide image processing according to embodiments of the disclosed technology. To aid in understanding the concepts of the present invention, system 200 will be described herein with reference to an ultrasound imaging system, such as may comprise a diagnostic ultrasound system utilized with respect to medical examinations and/or performing medical procedures or research.

In operation, a controller 221 controls transmission and reception of sampling signals for imaging operations. In the illustrated embodiment, controller 221 operates with a low frequency transmit beamformer 214, low frequency transmit/receive circuitry 212, and one or more low frequency transducer arrays 211 to generate one or more unfocused transmissions 201. Low frequency transmit/receive circuitry 212 can include A/D converters, programmable amplifiers, memory, filters, an FPGA for generating driving signals for the transducer elements, power amplifiers and other components known to those skilled in the art. In some embodiments, the low frequency transducer array 211, low frequency transmit/receive circuitry 212, and low frequency receive beamformer 213 operate to produce low frequency image frames using spatio-temporal plane wave beam forming techniques. The one or more low frequency transducer arrays 211 preferably comprise phased arrays as described above.

Controller 221 may comprise one or more processors, such as a central processing unit (CPU), microcontroller, digital signal processor (DSP), graphics processor (GPU), programmable gate array (PGA), application specific integrated circuit (ASIC), etc., operating under control of an instruction set or configured to operate as described herein. Controller 221 may additionally include a digital signal processor and computer readable media, such as random-access memory (RAM), read-only memory (ROM), magnetic memory, optical memory, etc., for storing instruction sets, operating parameters, and/or other useful data. Controller 221 controls the plane wave parameters for insonification of a volume in conjunction with the low frequency transmit beamformer 214 and low frequency transmit/receive circuitry 212.

The output of transmit/receive circuitry 212 of the illustrated embodiment supplies transmit signals to low frequency transducer array 211. In accordance with control provided by controller 221, the output from transducer array 211 is a sequence of plane waves that are used to insonify the contrast agent in a region of interest. The returned high frequency echo signals for the fired plane waves are received by the high frequency transducer array to produce a contrast agent image.

In some embodiments, echo data produced by tissue in response to the low frequency plane waves are received by the low frequency beamformer 213 and provided to the filtering and detection circuitry 231, such as a digital signal processor or ASIC, for further signal processing, such as filtering, object detection, etc. Echo signals produced in response to low frequency plane waves are processed by filtering and detection circuitry 231 and are provided to the compounding engine 232 (e.g. software in a DSP) for compounding to create a tissue image by combining echo data from plane waves transmitted in different directions.

In addition, the ultrasound imaging machine includes a high frequency transducer array 240, high frequency transmit/receive circuitry 242 and a high frequency plane wave transmit/receive beamformer 244. High frequency transmit/receive circuitry 242 can include A/D converters, programmable amplifiers, memory, filters, an FPGA for generating driving signals for the transducer elements, power amplifiers and other components known to those skilled in the art. If the high frequency transducer array is to be used to excite the contrast agent, then low frequency echo signals produced by the insonified contrast agent are received by the low frequency transducer array 211 that produces corresponding electronic signals that are processed by the low frequency receive circuitry. The signals are received, amplified, digitized and processed by the low frequency plane wave receive beamformer before being processed by the filtering and detection circuitry 231.

In some embodiments, the output of the HF transmit/receive circuitry 242 supplies transmit signals to high frequency transducer array 240. In accordance with control provided by controller 221, the output from high frequency transducer array 240 is a sequence of unfocused plane waves that are used to insonify the region of interest. The echo data produced by tissue in response to the high frequency plane waves are received by the high frequency beamformer 244 and provided to the filtering and detection circuitry 231 for further signal processing, such as filtering, object detection, etc. Echo signals produced in response to high frequency plane waves are processed by filtering and detection circuitry 231 and are provided to the compounding engine 232 for compounding or spatio-temporal beamforming to create a tissue image from the high frequency plane waves transmitted in different directions.

Scan conversion and back end processing unit 233 (e.g. software in a DSP or GPU) receives the tissue image and contrast agent image data and performs scan conversion and other image processing techniques so that the images can be viewed on a display 251. In addition, a combined tissue/contrast agent image can be synthesized in the back-end processing unit 233 by combining data from the tissue image with the contrast agent image as described above.

In some embodiments, the low and high frequency spatio-temporal beamformers, filtering and detection unit and scan conversion and back-end processing unit are all implemented in software executed by the programmable controller 221 executing appropriate software instructions. In other embodiments, these functions can be implemented with a digital signal processor, graphics processor, an ASIC or with programmed digital logic such as an FPGA.

User interface 261 may comprise any of a number of input and output devices useful for accepting data input, control parameters, operating instructions, etc. and/or outputting data, reports, status indicators, error messages, alarms, images, etc. For example, user interface 261 may comprise a keyboard, a pointer (e.g., mouse, digitizing tablet, touch pad, joystick, trackball, touch screen interface, etc.), a microphone, a speaker, a display, and/or the like. It should be appreciated that user interface 261 may comprise display 251 according to embodiments of the disclosed technology.

Figure 6:
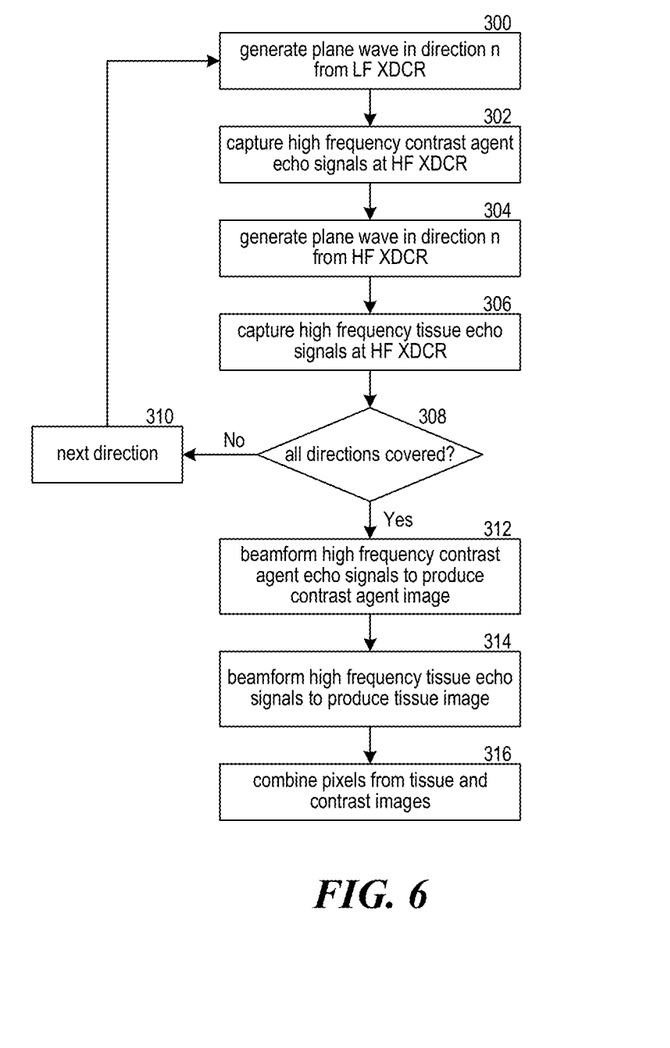
FIG. 6 is a flow chart of steps performed to create a combined tissue/contrast agent image from a number of steered low frequency plane waves in accordance with an embodiment of the disclosed technology.

FIG. 6 is a flow chart of steps performed by an ultrasound imaging machine to produce combined tissue/contrast agent images at high frame rates in accordance with an embodiment of the disclosed technology. Although the steps are described in a particular order for ease of explanation, it will be appreciated that the steps could be performed in a different order or that alternative steps could be performed in order to achieve the functionality described. As will be understood by those skilled in the art, the steps are preferably stored on a computer readable media such a RAM, ROM, EEPROM for execution by a programmable processor or are performed by configured digital logic such as an FPGA.

Beginning at 300, a processor instructs transmit electronics in the ultrasound imaging machine to generate an unfocused ultrasound wave such as a plane wave in a direction "n" from the low frequency transducer array(s). At 302, receive electronics in the ultrasound imaging machine capture the high frequency ultrasound echo signals produced by the high frequency transducer array in response to high frequency echoes from the contrast agent. At 304, the processor instructs the transmit electronics to generate a plane wave in the direction n from the high frequency transducer array. At 306, the receive electronics in the ultrasound imaging machine capture the high frequency echo signals produced by the high frequency transducer array in response to the high frequency echo signals from the tissue At 308, it is determined if all N plane wave transmit directions have been covered. If not, processing returns to 300 and low frequency plane waves are transmitted in the next direction. Once all the plane wave directions have been used, the system spatio-temporally beamforms the high frequency echo data from the contrast agent in the radio frequency domain to produce a contrast agent image frame at 312. At 314, the system spatio-temporally beamforms the high frequency echo data from the tissue in the radio frequency domain to produce a tissue image frame. At 316, pixels from the contrast agent image frame are combined or blended with the pixels from the tissue image frame to produce a combined tissue/contrast agent image frame. In some embodiments, radio frequency echo data is mixed to a lower frequency before spatio-temporally beamforming the echo data. In one embodiment, plane wave beamforming may be performed as described in *Ultrafast Imaging in Biomedical Ultrasound*, Mickael Tranter and Mathias Fink, IEEE Transactions on Ultrasonics, Ferroelectrics and Frequency Control, Vol. 61, No. 1, January 2014, which is herein incorporated by reference.

Figure 7:
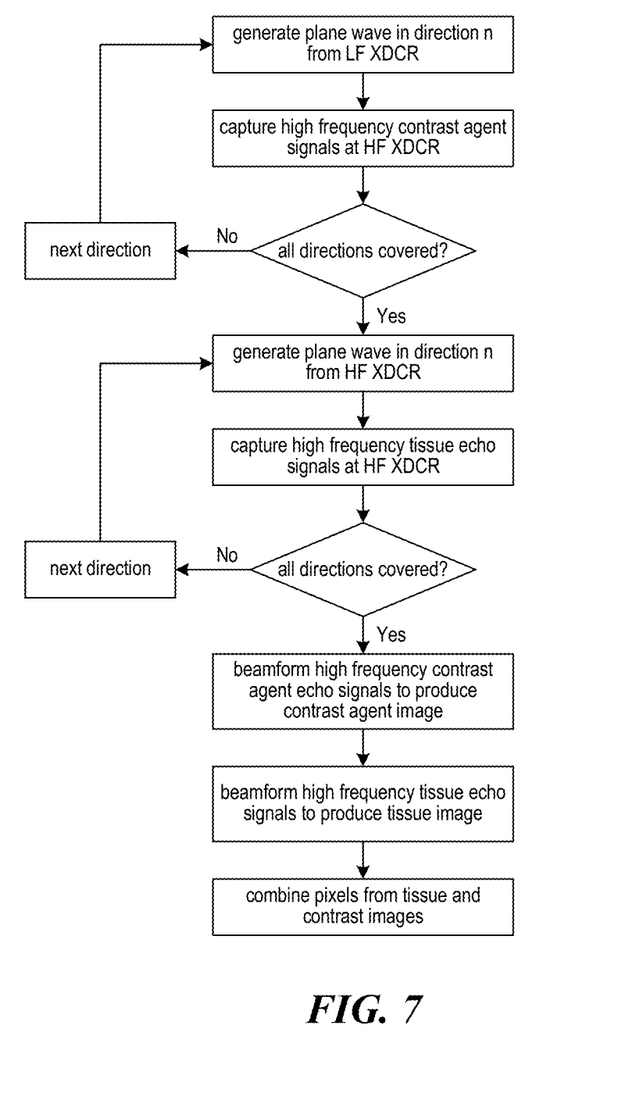
FIG. 7 is a flow chart of steps performed to create a combined tissue/contrast agent image from a number of steered low frequency plane waves in accordance with an embodiment of the disclosed technology.

In the embodiment described above, low frequency plane waves for exciting the contrast agent are interleaved with high frequency plane waves for tissue imaging. However, all the low frequency plane waves (e.g. 2-1000+) for contrast agent imaging can be transmitted first followed by the high frequency plane waves for tissue imaging or vice versa as shown in FIG. 7. Furthermore, while the number of different transmission directions is preferably greater than one, it will be appreciated that images can be made by insonifying the contrast agent/tissue in a single direction.

In some embodiments, the high frequency echo data from the contrast agent is further processed to determine Doppler color flow or Power Doppler characteristics of blood in the region of interest. Combined images can be created that show tissue and Doppler information or Doppler and contrast agent information. In some embodiments, a combined tissue/contrast agent image that also includes Doppler information (e.g. a tri-mode image) is created and displayed for the user.

In some embodiments, alpha blending or pixel substitution can be used to create the combined tissue/contrast agent image. As will be appreciated by those skilled in the art, each pixel location in the tissue image and contrast agent image is associated with a particular echo intensity. Therefore, pixels in the contrast agent image that represent contrast agent can be identified by their intensity and used to replace pixels in the same locations in the tissue image to produce the combined tissue/contrast agent image. In some embodiments, the pixels representing echoes from the contrast agent can be shown in a contrasting color compared to the gray-scale pixels representing tissue in order to highlight blood vessels or moving blood flow.

From the foregoing, it will be appreciated that specific embodiments of the invention have been described herein for purposes of illustration, but that various modifications may be made without deviating from scope of the invention. For example, the operating frequency of the low frequency transducer array and the high frequency transducer array can be modified depending on a number of factors such as the depth or type of tissue to be imaged. In addition, the low frequency transducer array(s) can be used to produce tissue images at lower frequencies from echo data created by the tissue in response to insonification by the low frequency plane waves. Alternatively, the low frequency transducer array can capture echo signals at sub-harmonics of high frequency insonification plane waves generated by the high frequency transducer array. Ultrasound plane waves produced by the high frequency transducer array may be transmitted in different directions than the directions of the plane waves transmitted by the low frequency transducer array. Alternatively, the high frequency transducer array may only transmit plane waves in a single direction to produce a tissue image without spatial compounding. In yet another embodiment, only the low frequency transducer generates plane waves and the high frequency transducer array can use conventional beamline transmit and receive imaging techniques to produce a tissue image. Accordingly, the invention is not limited except as by the appended claims.

We claim:

1. A dual frequency ultrasound imaging system, comprising:
   a high frequency transducer array configured to transmit ultrasound into an imaging region and to receive high frequency ultrasound echo signals from the imaging region;
   one or more low frequency transducer arrays configured to transmit unfocused ultrasound plane waves into the imaging region of the high frequency transducer array to insonify contrast agent in the imaging region such that the plane waves of each of the one or more low frequency transducers intersect at an angle with the imaging region, wherein the plane waves are interleaved with ultrasound transmitted and received by the high frequency transducer array such that echo signals transmitted by the high frequency transducer do not interfere with echo signals transmitted by the low frequency transducer; and
   signal processing circuitry for:
      processing high frequency ultrasound echo signals from tissue created in response to high frequency ultrasound signals transmitted by the high frequency transducer array;
      creating a tissue image from the high frequency ultrasound echo signals received from tissue;
      processing high frequency ultrasound echo signals created in response to the contrast agent being insonified by the unfocused ultrasound from the one or more low frequency transducer arrays;

creating a contrast agent image from the processed high frequency ultrasound echo signals created in response to the contrast agent; and creating a combined tissue/contrast agent image with data from the tissue image and the contrast agent image.

2. The dual frequency ultrasound imaging system of claim 1, wherein the one or more low frequency transducer arrays are configured to transmit plane waves at multiple angles and the contrast agent image is created from spatio-temporally beamformed echo signals combined with radio frequency echo data.

3. The dual frequency ultrasound imaging system of claim 1, wherein the high frequency transducer array is configured to transmit plane waves at multiple angles into the imaging region.

4. The dual frequency ultrasound imaging system of claim 3, wherein the tissue image is created from spatio-temporally beamformed echo signals combined with radio frequency echo data from the high frequency ultrasound transmitter.

5. The dual frequency ultrasound imaging system of claim 1, wherein the combined tissue/contrast agent image is created using one of alpha blending and pixel substitution.

6. A dual frequency transducer comprising: a high frequency central array that is configured to be used as a receiver and one or more flanking low frequency transducer arrays configured to transmit unfocused low frequency ultrasound signals which intersect at an angle with an imaging region of the high frequency central array to insonify contrast agent in a region of interest, wherein the high frequency central array is positioned to receive echo signals from the contrast agent excited by the unfocused ultrasound signals from the one or more low frequency transducer arrays, and the one or more flanking low frequency transducer arrays are configured to transmit unfocused ultrasound signals that are interleaved with ultrasound transmitted and received by the high frequency transducer array such that echo signals transmitted by the high frequency transducer do not interfere with echo signals transmitted by the low frequency transducer.

7. The dual frequency transducer of claim 6, wherein the one or more flanking low frequency transducer arrays are configured to transmit plane waves at multiple angles and the contrast agent image is created from spatio-temporally beamformed echo signals combined with radio frequency echo data.

8. The dual frequency transducer of claim 6, wherein the high frequency transducer array is configured to transmit plane waves at multiple angles into the imaging region.

9. The dual frequency ultrasound imaging system of claim 6, wherein the one or more flanking low frequency transducer arrays transmit plane waves.

10. A dual frequency ultrasound imaging system, comprising:
a high frequency transducer array;
one or more low frequency transducer arrays configured to transmit ultrasound plane waves that intersect at an angle with an imaging region of the high frequency transducer array, wherein the plane waves are interleaved with ultrasound transmitted and received by the high frequency transducer array such that echo signals transmitted by the high frequency transducer do not interfere with echo signals transmitted by the low frequency transducer;

signal processing circuitry for:
controlling the high frequency transducer array or the one or more low frequency transducer arrays to transmit unfocused ultrasound signals into a focal region to insonify contrast agent in the imaging region;
controlling the other of the one or more low frequency transducer arrays or the high frequency transducer array to receive echo signals from the insonified contrast agent;
producing a contrast agent image from the echo signals from the insonified contrast agent;
producing a tissue image from echo signals received from tissue in the imaging region; and
producing a combined tissue/contrast agent image from the contrast agent image and the tissue image.

11. The dual frequency ultrasound imaging system of claim 10, wherein the tissue image is created from ultrasound transmitted and received by the high frequency transducer array.

12. The dual frequency ultrasound imaging system of claim 10, wherein the tissue image is created from ultrasound transmitted and received by the one or more low frequency transducer arrays.

13. The dual frequency ultrasound imaging system of claim 10, wherein the unfocused ultrasound is transmitted by the one or more low frequency transducer arrays and the contrast agent image is created from high frequency ultrasound array echoes received by the high frequency transducer array.

14. The dual frequency ultrasound imaging system of claim 10, wherein the unfocused ultrasound is transmitted by the high frequency transducer array and the contrast agent image is created from low frequency ultrasound echoes received by the one or more low frequency transducer arrays.

15. The dual frequency ultrasound imaging system of claim 10, wherein the unfocused ultrasound are planewaves.

16. The dual frequency ultrasound imaging system of claim 10, wherein the unfocused ultrasound are spherical waves.

17. The dual frequency ultrasound imaging system of claim 10, wherein the high frequency central array transmits unfocused ultrasound signals.

18. The dual frequency ultrasound imaging system of claim 17, wherein the unfocused ultrasound are planewaves.

19. The dual frequency ultrasound imaging system of claim 17, wherein the unfocused ultrasound are spherical waves.

20. The dual frequency ultrasound imaging system of claim 10, wherein the combined tissue/contrast agent image is produced using one of alpha blending and pixel substitution.

* * * * *